United States Patent [19]

Bastioli et al.

[11] Patent Number: 5,004,817

[45] Date of Patent: Apr. 2, 1991

[54] POLYOXYALKYLENE-ETHER DERIVATIVES HAVING ORGANIC ACID END-GROUPS, THEIR ALKYL ETHERS AND THEIR ALKALI METAL AND ALKALINE-EARTH METAL SALTS

[75] Inventors: Catia Bastioli, Novara; Salvatore Garlisi, Vercelli; Dario Fornara, Novara; Vittorio Bellotti, Fontaneto D'Agogna, all of Italy

[73] Assignee: Montefibre, S.p.A., Milan, Italy

[21] Appl. No.: 315,568

[22] Filed: Feb. 27, 1989

[30] Foreign Application Priority Data

Feb. 29, 1988 [IT] Italy .............................. 19576 A/88

[51] Int. Cl.$^5$ ...................... C07D 303/12; C07C 65/21
[52] U.S. Cl. ........................ 549/557; 549/551; 549/555; 560/254; 560/255; 560/103; 560/106; 560/107; 560/31; 560/32; 560/163; 560/164; 562/427; 562/429; 562/430; 562/434; 562/437; 562/426; 562/433; 562/466; 562/438; 562/473; 562/474
[58] Field of Search ............... 562/473, 474, 434, 437, 562/438, 427, 429, 430, 426, 433, 466; 549/551, 557, 555; 560/254, 255, 103, 107, 106, 31, 32, 163, 164

[56] References Cited

U.S. PATENT DOCUMENTS 3,494,939  2/1970  Smith .................................. 562/473
4,486,561  12/1984  Chung et al. ........................ 524/102

FOREIGN PATENT DOCUMENTS 295673  3/1954  Switzerland .......................... 562/473
299190  8/1954  Switzerland .......................... 562/473

OTHER PUBLICATIONS

Yoshizawa, Y. et al., *Chemical Abstracts* 83: 164876e, "Modified Poly(Ether Esters)," (1975).
Kawase, A., *Chemical Abstracts* 77: 36224e, "Polyesters with Improved Dyeability," (1972).

*Primary Examiner*—Richard L. Raymond
*Assistant Examiner*—Mark W. Russell
*Attorney, Agent, or Firm*—Morgan & Finnegan

[57] ABSTRACT

Compounds having the formula (I):

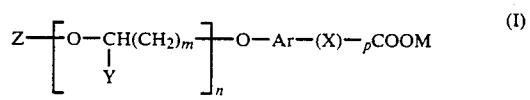

wherein:
- M is an alkali or alkaline-earth metal or a $C_1$–$C_{18}$ alkyl group;
- X is a group selected from —$CH_2$—, —CO—, —$CH_2$—CO—, —$CH(CH_3)$—CO—,
- p is 0 or 1;
- Ar is a simple or condensed aromatic ring or Ar represents two or more aromatic nuclei bonded either by a simple bond or by an —O—, —S—, —$SO_2$—, —SO—, —CO—, —CS—, or —NH— group;
- y is H or $CH_3$;
- m is 1 when Y=—$CH_3$, or an integer from 1 to 5 (including both values) when Y=H; n is a number ranging from 1 to 500 (including both values); and
- Z is H; a $C_1$–$C_{18}$ alkyl; benzyl; glycidyl; acetyl; allyl; —CO—NH—R or —CO—NH—$R_1$—NCO group.

9 Claims, No Drawings

POLYOXYALKYLENE-ETHER DERIVATIVES HAVING ORGANIC ACID END-GROUPS, THEIR ALKYL ETHERS AND THEIR ALKALI METAL AND ALKALINE-EARTH METAL SALTS

DESCRIPTION OF THE INVENTION

The present invention relates to polyoxyalkylene-ether derivatives having organic acid end-groups of formula:

$$HO-Ar-(X)_p COOM \qquad (II)$$

and more particularly to compounds having formula (I):

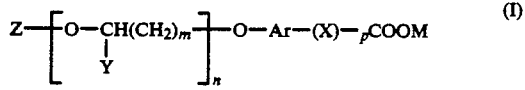

wherein

M is an alkali or alkaline-earth metal or a $C_1$–$C_{18}$ alkyl group;

X is a group selected from

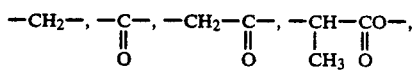

p is 0 or 1;

Ar is a simple or condensed aromatic ring having from 6 to 14 carbon atoms, optionally substituted with halogen atoms, $C_1$–$C_8$ alkyl, $C_1$–$C_8$ alkoxy, or nitro groups and the like; or Ar represents two or more aromatic nuclei bonded either by a simple bond or by an —O—, —S—, —SO$_2$—, —SO—, —CO—, —CS—, or —NH— group;

Y is H or $CH_3$;

m is 1, when Y=—$CH_3$, or an integer from 1 to 5 (including both values) when Y=H;

n is a number ranging from 1 to 500 (including both values); and

Z is selected from H; a $C_1$–$C_{18}$ alkyl; benzyl; allyl;

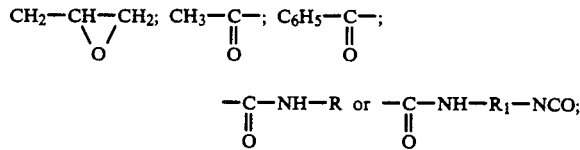

wherein R is a non-substituted phenyl group or a phenyl group substituted with halogen atoms or a $C_{10}$–$C_{40}$ alkyl group; and $R_1$ is a non-substituted phenylene group or a phenylene group substituted with halogen atoms or a $C_{10}$–$C_{40}$ alkylene group.

Such compounds, on account of their particular molecular structure, may be used as plasticizers or as nucleating agents for polyester resins, because the structures which confer such properties are bound together in the same molecule.

Alkali metal salts of carboxylic acids and in particular of benzoic acid (as nucleating agents for PET) are known from the prior art (see for instance U.S. Pat. No. 4,486,561 and and JP-A-59/230,048).

Such formulations, however, generally require the joint use of other additives, and in particular of plasticizers, in order to act both on the crystallization temperature in the melted state, on the cold crystallization temperature and on the glass transition temperature of the amorphous phase.

The compounds of formula (I) may be represented as a saline nucleating agent, which is bound chemically to a polymeric oxyalkylene chain, an alcoholic terminal group having been made functional.

By using these compounds one may now obtain the final properties for a good molding of the polyester resin because, besides obtaining the required degree of plasticization due to the presence of the polyoxyalkylene chain, this chain, soluble in the resin, promotes a better dispersion of the nucleating agent, with formation of a homogeneous microspherulitic crystalline structure.

Moreover the extremity of the polyoxyalkylene chain made functional by ether, ester, epoxide or urethane groups, allows variations as to uses, according to the desired applications and to the required final properties.

A few of the possible products answering to formula (I) are those in which Z, Y, Ar, X, Me, m and n have the meanings set forth in the following Table.

TABLE

| | Z | Y | m | n | Ar | X* | Na |
|---|---|---|---|---|---|---|---|
| (1) | —H | H | 1 | about 20 |  | - | Na |
| (2) | —H | $CH_3$ | 1 | about 20 | 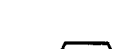 | - | Na |
| (3) |  | H | 1 | about 90 |  | - | Na |

TABLE-continued
| Z | Y | m | n | Ar | X* | Na |
|---|---|---|---|---|---|---|
| (4) −CH₂−CH−CH₂ (epoxide) | CH₃ | 1 | about 90 | 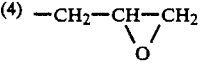 | - | Na |
| (5) −C(=O)−CH₃ | H | 1 | about 90 |  | - | Na |
| (6) −C(=O)−CH₃ | CH₃ | 1 | about 90 | 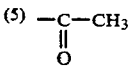 | - | Na |
| (7) −C(=O)− | H | 1 | about 90 | 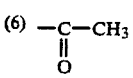 | - | Na |
| (8) −C(=O)− | CH₃ | 1 | about 90 | 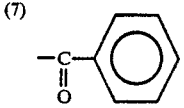 | - | Na |
| (9) −CH₃ | H | 1 | about 90 |  | - | Na |
| (10) −CH₃ | CH₃ | 1 | about 90 | 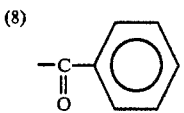 | - | Na |
| (11) −C₂H₅ | H | 1 | about 90 |  | - | Na |
| (12) −C₂H₅ | CH₃ | 1 | about 90 | 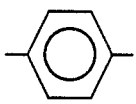 | - | Na |
| (13) −C₃H₇ | H | 1 | about 90 | 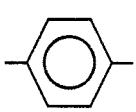 | - | Na |
| (14) −C₃H₇ | CH₃ | 1 | about 90 | 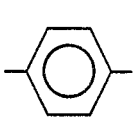 | - | Na |
| (15) −CH₂−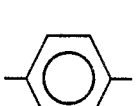 | H | 1 | about 90 | 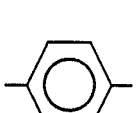 | - | Na |
| (16) −CH₂−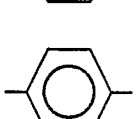 | CH₃ | 1 | about 90 | 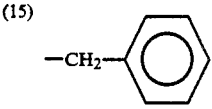 | - | Na |

TABLE-continued
| | Z | Y | m | n | Ar | X* | Na |
|---|---|---|---|---|---|---|---|
| (17) | $-\underset{\underset{O}{\|}}{C}-NH-C_{18}H_{37}$ | H | 1 | about 20 | 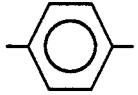 | - | Na |
| (18) | $-\underset{\underset{O}{\|}}{C}-NH-C_{18}H_{36}-NCO$ | H | 1 | about 20 |  | - | Na |
| (19) | —H | H | 1 | about 20 | 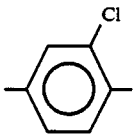 Cl | - | Na |
| (20) | —H | H | 1 | about 20 | 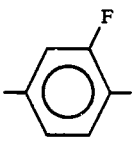 F | - | Na |
| (21) | —H | H | 1 | about 20 | 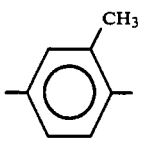 $CH_3$ | - | Na |
| (22) | —H | H | 1 | about 20 | 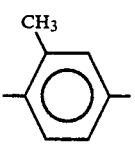 $CH_3$ | - | Na |
| (23) | —H | H | 1 | about 20 | 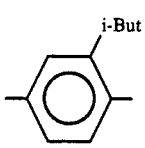 i-But | - | Na |
| (24) | —H | H | 1 | about 20 | 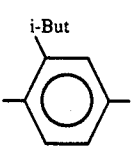 i-But | - | Na |
| (25) | —H | H | 1 | about 20 | 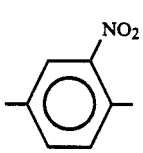 $NO_2$ | - | Na |
| (26) | —H | H | 1 | about 20 | 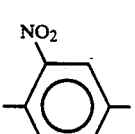 $NO_2$ | - | Na |
| (27) | —H | H | 1 | about 20 | 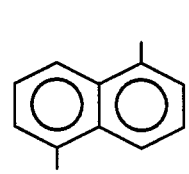 | - | Na |

TABLE-continued

| | Z | Y | m | n | Ar | X* | Na |
|---|---|---|---|---|---|---|---|
| (28) | —H | H | 1 | about 20 | 2,6-naphthalene | - | Na |
| (29) | —H | H | 1 | about 20 | —C₆H₄—O—C₆H₄— | - | Na |
| (30) | —H | H | 1 | about 20 | —C₆H₄—CO—C₆H₄— | - | Na |
| (31) | —H | H | 1 | about 20 | —C₆H₄—S—C₆H₄— | - | Na |
| (32) | —H | H | 1 | about 20 | —C₆H₄—SO₂—C₆H₄— | - | Na |
| (33) | —H | H | 1 | about 20 | —C₆H₄—CS—C₆H₄— | - | Na |
| (34) | —H | H | 1 | about 20 | —C₆H₄—NH—C₆H₄— | - | Na |
| (35) | —CH₂—CH(O)CH₂— (glycidyl) | H | 1 | about 90 | —C₆H₄— | —CO— | Na |
| (36) | —H | H | 1 | about 20 | —C₆H₄— | —CO— | Na |
| (37) | —CH₂—CH(O)CH₂— (glycidyl) | H | 1 | about 90 | —C₆H₄— | —CH₂—CO— | Na |
| (38) | —H | H | 1 | about 20 | —C₆H₄— | —CH₂—CO— | Na |
| (39) | —H | H | 1 | about 90 | —C₆H₄— | —CH(CH₃)—CO— | Na |
| (40) | —H | H | 1 | about 20 | —C₆H₄— | —CH(CH₃)—CO— | Na |

TABLE-continued

| Z | Y | m | n | Ar | X* | Na |
|---|---|---|---|---|---|---|
| (41) —H | H | 2 | about 20 |  | - | Na |
| (42) —H | H | 3 | about 20 |  | - | Na |
| (43) —H | H | 1 | about 20 | 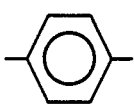 | —CH$_2$— | Na |

*hyphen (-) denotes the case where p = 0, namely when X represents a single bond.

Although all these products may be used as nucleating agents and as plasticizers of polyester resins, in particular the ones based on PET, a particular preference is given for this purpose to those products of formula (I) wherein Ar is

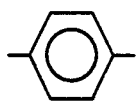

represents a single bond, namely the polyoxyalkyleneether derivatives having p-hydroxybenzoic acid endgroups, their alkali and alkaline earth metal salts, and their esters.

The compounds having formula (I) are generally prepared by the usual methods, starting from an alkyl ester of an acid having formula (II):

HO—Ar—(X)—$_p$COOH      (II)

wherein Ar, X and p have the meanings as specified hereinbefore.

In a first stage of the preparation, such esters are reacted in an autoclave with an alkylene oxide in the presence of an alkali, at a temperature of 130° C. and at a pressure of about 3 atmospheres.

Afterwards the thus-obtained product is saponified with an alkali metal hydroxide in order to obtain the salt acid, if the product is desired in that form.

The third stage of the preparation resides in making the OH end-groups of the polyoxyalkylene chains functional, according to known techniques.

A few examples relating to the preparation of products answering to formula (I) will be reported hereinafter, merely by way of illustration, but not of limitation, in order still better to understand the invention and to facilitate carrying it out.

The number of units of ethylene oxide introduced into the molecules of the compounds, as prepared hereinafter and reported in the examples, has to be considered, obviously, as an average value. By changing the ratios between the ethylene oxide and the remaining reagents, according to known methods, it is possible to insert an oxyethylene chain of whichever length might be desired.

EXAMPLE 1

Preparation of ethyl-para-(hydroxy-polyethyleneoxy)benzoate (about 90 units of ETO)

A mixture consisting of 185.5 g of ethyl para-hydroxybenzoate, 6.2 g of potassium hydroxide flakes, and 425.0 g of xylene, was heated under stirring at 100° C., thereby obtaining a slightly cloudy solution.

Then the solution was sucked into an autoclave and the system was degassed from oxygen by means of repeated vacuum/nitrogen washings.

After having brought the temperature to 130° C. under stirring, one adds ethylene oxide for a total amount of 4,392.5 g, while keeping the temperature at 130° C. and the pressure at about 3 atmospheres. The reaction time was about 6 hours.

When the addition of the ethylene oxide was over, after exhaustion of said ethylene oxide the system was kept under vacuum for about 15 minutes. One cooled down to 90° C., the autoclave was unloaded, and the reaction system was neutralized with glacial acetic acid (6.6 g).

The thus obtained reaction mixture was conveyed into a 6 liter reactor, equipped with an anchor stirrer, a thermometer, and a Liebig cooler. After having heated at about 100° C., vacuum was applied (50 residual Hg mm).

About 350 g of xylene were distilled (the remainder, with respect to the amount that had been loaded, had already been removed in the vacuum stage which followed the oxyethylation).

When the distillation was over, vacuum was discontinued, one cooled to about 80° C. and then unloaded.

One thus obtained about 4700 g of ethylene para(hydroxy-polyethyeleneoxy)-benzoate, containing about 90 units of ETO, having the following characteristics:

| acid number | 1.1 |
|---|---|
| hydroxyl number | 24.1 |
| saponification number | 13.8 |

EXAMPLE 2

Preparation of sodium para-(hydroxy-polyethyleneoxy)-benzoate (about 90 units of ETO).

500 g of ethyl para-(hydroxy-polyethylene)-benzoate (about 90 units of ETO), obtained according to Example 1, and 16.5 g of 30% sodium hydroxide were loaded into a 1 liter reactor equipped with an anchor stirrer, a thermometer, and a bubble cooler. After having brought the internal temperature to 80° C. under stirring, the system was kept at that temperature for 1 hour.

After having replaced the bubble cooler by a Liebig cooler, vacuum was applied (50 residual Hg mm). After having kept the reaction mixture under these conditions for half an hour, during which time about 12 g of water and ethanol were distilled, vacuum was discontinued and one cooled down to 50° C., after which the reactor was unloaded.

One thus obtained about 500 g of a product having the following characteristics:

| acid number | 0.2 |
|---|---|
| hydroxyl number | 36.3. |

EXAMPLE 3

Preparation of sodium para-(glycidoxy-polyethyleneoxy)benzoate (about 90 units of ETO)

300 g of sodium para-(hydroxy-polyethyleneoxy)benzoate (about 90 units of ETO), obtained according to the procedure described in Example 2, and 3.3 g of ROLCRIL®S (lauryl-dimethyl-benzyl ammonium chloride at 50% concentration in water) were loaded into a 0.5 liter reactor equipped with an anchor stirrer, a dropping funnel, a thermometer, and a bubble cooler.

After having brought the internal temperature to 60° C. under stirring, 7.9 g of sodium hydroxide drops were added in 5 minutes, after which the system was kept for 1 hour under the same conditions.

One then started to drip 18 g of epichlorohydrin at such a rate that the whole amount was introduced in 1 hour. Afterwards the reaction mixture was kept for a further 6 hours under the same conditions.

Then the internal temperature was increased to 80° C., the bubble cooler was replaced by a Liebig cooler, and vacuum was applied (50 residual Hg mm). The system was kept under these conditions for 1 hour, during which time a small amount of water distilled, and afterwards the reactor was unloaded.

One thus obtained about 320 g of a product having the following characteristics:

| Aspect at 20° C. | yellow flakes |
|---|---|
| melting point | +55° C. |
| acid number | 0.4 |
| saponified acid number | 14.4 |
| epoxide equivalent | 1902.7 |
| NaCl (%) | 3.5 |
| H$_2$O (%) | 0.3 |

EXAMPLE 4

Preparation of sodium para-(acetyloxy-polyethyleneoxy)benzoate (about 90 units of ETO).

200 g of sodium para-(hydroxy-polyethyleneoxy)benzoate (about 90 units of ETO), obtained according to Example 2, were located into a 0.5 liter reactor equipped with an anchor stirrer, a dropping funnel, a thermometer, and a bubble cooler. After having brought the internal temperature to 95° C. under stirring, one started to drip 15.3 g of acetic anhydride, allowing all the acetic anhydride to flow into the reactor in 45 minutes. When the addition was over, the reaction mixture was kept at 95° C. and under stirring for 2

Then the bubble cooler was replaced by a Liebig cooler and vacuum was applied (50 residual Hg mm).

The internal temperature was brought to 140° C. The acetic acid began to distill at 130° C.

The system was kept at 140° C. until the acid number of the mixture was ≦3 (the required time was about 2 hours). Vacuum was discontinued, one cooled to 60° C. and then unloaded.

One thus obtained about 205 g of a product having the following characteristics:

| Aspect at 20° C. | beige flakes |
|---|---|
| melting point | 50° C. |
| acid number | 2.2 |
| hydroxyl number | 0.5 |
| saponified acid number | 14.0 |

EXAMPLE 5

Preparation of sodium para-(benzyloxy-polyethyleneoxy)benzoate (about 90 units of ETO).

200 g of sodium para-(hydroxy-polyethyleneoxy)benzoate (about 90 units of ETO), obtained according to Example 2, and 2.5 g of ROLCRIL®S were loaded into a 0.5 liter reactor, equipped with an anchor stirrer, a dropping funnel, a thermometer, and a bubble cooler. The internal temperature was brought to 60° C. under stirring; then 5.6 g of sodium hydroxide drops were added in 5 minutes and the reaction mixture was kept at 60° C. and under stirring for 1 hour.

One then started to drip 19.2 g of benzyl chloride, allowing the whole amount to be introduced in 1 hour. The system was kept under the same conditions for a further 6 hours, and afterwards the internal temperature was brought to 80° C. The bubble cooler was replaced by a Liebig cooler and a vacuum was applied (50 residual Hg mm). The system was kept under these conditions for 1 hour, during which time a small amount of water distilled, and afterwards one unloaded.

One thus obtained about 220 g of a product having the following characteristics:

| Aspect of 20° C. | yellow flakes |
|---|---|
| melting point | 51° C. |
| acid number | 0.1 |
| saponified acid number | 13.9 |
| hydroxyl number | 17.4 |
| NaCl % | 4.1 |

EXAMPLE 6

Preparation of ethyl para-(hydroxy-polyethyleneoxy)benzoate (about 20 units of ETO)

A mixture consisting of 368.1 g of ethyl para-hydroxybenzoate, 9.0 g of potassium hydroxide flakes, and 858.6 g of xylene, was heated, under stirring at about 100° C., thereby obtaining a slightly cloudy solution. Then the solution was sucked into an autoclave and the system was degassed from oxygen by means of repeated washings vacuum-nitrogen.

After having brought the temperature to 130° under stirring, one started to add ethylene oxide, for a total amount of 1773.3 g, by keeping the temperature at 130° C. and the pressure at about 3 atmospheres. The reaction time was about 3 hours. When the addition of ethylene oxide was over, after exhaustion of said ethylene oxide the system was kept under vacuum for 15 minutes and cooled to 90° C., whereupon the autoclave was unloaded and the reaction system was neutralized with glacial acetic acid (9.6 g).

The thus obtained reaction mixture was conveyed into a 4 liter reactor, equipped with an anchor stirrer, a thermometer and a Liebig cooler. After having heated at about 100° C., vacuum was applied (50 residual Hg mm).

About 590 g of xylene distilled (the remainder, with respect to the amount that had been loaded, had already been removed in the vacuum step which followed the ethoxylation). When the distillation was over, vacuum was discontinued, whereupon one cooled to about 80° C. and unloaded.

One thus obtained about 2100 g of a product having the following characteristics:

| | |
|---|---|
| Acid number | 2.6 |
| saponification number | 59.5 |
| hydroxyl number | 61.1 |

EXAMPLE 7

Preparation of sodium para-(hydroxy-polYethyleneoxy)benzoate (about 20 units of ETO)

220 g of ethyl para-(hydroxy-polyethyleneoxy)-benzoate (about 20 units of ETO), obtained according to Example 6, and 31.1 of 30% sodium hydroxide were loaded into a 0.5 liter reactor, equipped with an anchor stirrer, a thermometer, and a bubble cooler. After having brought the internal temperature to 80° C. under stirring, this temperature was kept for 1 hour. The product became more and more pasty, so that stirring became difficult. After 1 hour, one replaced the bubble cooler by a Liebig cooler and vacuum was applied (50 residual Hg mm). The reaction mixture was kept under this condition for 1 hour, during which time about 20 g of water and ethanol distilled, after which vacuum was discontinued, the mixture cooled, and the reactor unloaded.

One thus obtained about 220 g of a product having the following characteristics:

| | |
|---|---|
| Aspect of 20° C. | pasty mass |
| alkali number | 0.7 |
| hydroxyl number | 90.7 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Compounds having the formula (I):

$$Z \left[ O - \underset{Y}{\underset{|}{CH}}(CH_2)_m \right]_n O - Ar - COOM \quad (I)$$

wherein:

M is an alkali or alkaline-earth metal of a $C_1$–$C_{18}$ alkyl group;

Ar is a simple or condensed aromatic ring having from 6 to 14 carbon atoms, optionally substituted with halogen atoms, $C_1$–$C_8$ alkyl, $C_1$–$C_8$ alkoxy, nitro groups; or Ar represents two or more aromatic nuclei bound either by a simple bond or by an —O—, —S—, —SO$_2$—, —SO—, —CO—, —CS—, or —NH— group;

Y is H or $CH_3$;

m is 1 when Y=—$CH_3$, or an integer from 1 to 5, including both values, when Y=—$CH_3$, or an integer from 1 to 5, including both values, when Y=H;

n is a number ranging from 20 to 500 including both values; and

Z is selected from the class consisting of H; a $C_1$–$C_{18}$ alkyl, benzyl; allyl;

$$CH_2-CH-CH_2; \quad CH_3-\underset{\underset{O}{\|}}{C}-; \quad C_6H_5-\underset{\underset{O}{\|}}{C}-; \quad -\underset{\underset{O}{\|}}{C}-NH-R; \text{ and}$$
$$\diagdown O \diagup$$

$$-\underset{\underset{O}{\|}}{C}-NH-R_1-NCO;$$

wherein R is a non-substituted phenyl group or a phenyl group substituted with halogen atoms or a $C_{10}$–$C_{40}$ alkyl group; and $R_1$ is a non-substituted phenylene or a phenylene substituted with halogen atoms or a $C_{10}$–$C_{40}$ alkylene group.

2. Compounds according to claim 1, wherein Ar is a phenylene group.

3. Compounds according to claim 2, wherein Z is selected from the class consisting of —H, $$-CH_2-CH-CH_2, \quad CH_3-\underset{\underset{O}{\|}}{C}-, \quad C_6H_5-\underset{\underset{O}{\|}}{C}-,$$
$$\diagdown O \diagup$$

4. Compounds according to claim 1, 2 or 3, wherein n is about 90.

5. Sodium para-(hydroxy-polyethyleneoxy)-benzoate having the formula:

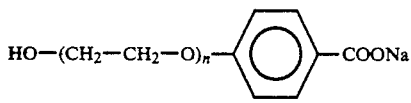
wherein n is about 90.
6. Sodium para-(glycidoxy-polyethyleneoxy)-benzoate having formula:
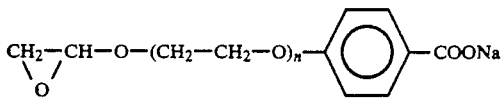
wherein n is about 90.
7. Sodium para-(acetyloxy-polyethyleneoxy)-benzoate having formula:
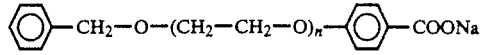
wherein n is about 90.
8. Sodium para-(benzyloxy-polyethyleneoxy)-benzoate having formula:
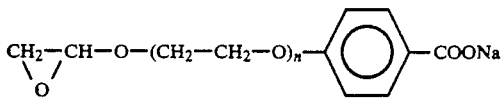
wherein n is about 90.
9. Sodium para-(hydroxy-polyethyleneoxy)-benzoate having formula;
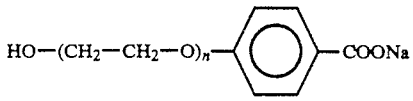
wherein n is about 20.
* * * * *